United States Patent

Kiesele

[11] Patent Number: 5,547,554
[45] Date of Patent: Aug. 20, 1996

[54] ELECTROCHEMICAL MEASURING CELL HAVING A GAS-PERMEABLE HOUSING

[75] Inventor: Herbert Kiesele, Lübeck, Germany

[73] Assignee: Drägerwerk Aktiengesellschaft, Lübeck, Germany

[21] Appl. No.: 321,879

[22] Filed: Oct. 14, 1994

[30] Foreign Application Priority Data

Oct. 18, 1993 [DE] Germany ............... 43 35 409.2

[51] Int. Cl.⁶ ............................................. G01N 27/404
[52] U.S. Cl. ............................................. 204/415
[58] Field of Search ........................... 204/153.17, 415

[56] References Cited

U.S. PATENT DOCUMENTS

| Re. 24,222 | 9/1956 | Patnode et al. | 204/435 |
|---|---|---|---|
| 2,595,042 | 4/1952 | Wyllie | 204/435 |
| 3,577,332 | 5/1971 | Porter et al. | 204/415 |
| 3,708,411 | 1/1973 | Vanslette | 204/419 |
| 4,051,006 | 9/1977 | Neti et al. | 204/415 |
| 4,100,048 | 7/1978 | Pompei | 204/415 |
| 4,126,531 | 11/1978 | Porter et al. | 204/415 |
| 5,314,605 | 5/1994 | Mattiessen | 204/415 |
| 5,336,390 | 8/1994 | Busack et al. | 204/415 |

FOREIGN PATENT DOCUMENTS 3542261  6/1987  Germany.

*Primary Examiner*—T. Tung
*Attorney, Agent, or Firm*—Walter Ottesen

[57] ABSTRACT

The invention is directed to an electrochemical measuring cell for detecting gaseous constituents in air. The measuring cell includes a measuring electrode and a counter electrode accommodated in a housing. The housing includes an electrolyte chamber and the electrolyte is in liquid contact with the electrodes. The measuring electrode is in diffusion contact with the gas constituents to be detected via a gas-permeable membrane which is impermeable to the electrolyte. The measuring cell is improved so that an effective pressure equalization between the electrolyte chamber and the ambient is made possible in the context of a simple assembly of the housing. For this purpose, the housing jacket surrounding the electrolyte chamber has at least one breakthrough. The electrolyte chamber is separated from the ambient by a gas-permeable stop disposed in the breakthrough. This stop is impermeable to the electrolyte.

10 Claims, 2 Drawing Sheets

ELECTROCHEMICAL MEASURING CELL HAVING A GAS-PERMEABLE HOUSING

FIELD OF THE INVENTION

The invention relates to an electrochemical measuring cell for detecting gaseous constituents in air. The measuring cell accommodates a measuring electrode and a counter electrode within a housing. The electrodes are connected to an electrolyte via a liquid connection and, of these electrodes, the measuring electrode is brought into diffusion contact with the gaseous constituents to be detected via a gas-permeable membrane which is impermeable to the electrolyte.

BACKGROUND OF THE INVENTION

An electrochemical measuring cell of the kind referred to above is disclosed in U.S. Pat. No. 4,051,006. In this known measuring cell, a cylindrical round body having two end faces is made of polytetrafluoroethylene. Each of the two end faces is provided with a ring-shaped cover and a clamping ring. The cover and clamping ring at each end clamp a porous membrane which is permeable for gaseous constituents but is impermeable for the electrolyte disposed in the inner space of the housing. The gaseous constituent of the air to be detected communicates with the membrane via a diffusion path and, in this way, allows the gas to be detected to enter into the inner space filled with the electrolyte. The inner space likewise accommodates the measuring electrode in direct proximity to the diffusion membrane. The electrolyte is located in a hydrophilic fill body or filler made of glass wool and is in liquid contact between the measuring electrode and the counter electrode. The counter electrode is disposed within the filler and is completely surrounded by the electrolyte liquid.

The membrane clamped by the ring is likewise permeable to the gaseous constituents; however, the membrane is impermeable for the electrolyte. The membrane functions to output the gaseous components to the ambient which are formed during the electrochemical reaction.

A problem occurring with the known electrochemical measuring cell has to do with equalizing the pressure between the chamber or the interior space of the housing which holds the electrolyte and the ambient. The electrolyte chamber is generally only partially filled because the electrolyte volume changes with ambient conditions (moisture, temperature). For this reason, a gas bubble is normally present in the interior space of the sensor. If the ambient pressure drops, for example, during transport in an aircraft, then an overpressure occurs in the sensor which can only be reduced without difficulty if at least one of the gas-permeable membranes is not covered by the electrolyte. This is possible in the known measuring cell only under favorable conditions with a perpendicular orientation and without an electrolyte surplus. However, if the membranes are covered by the electrolyte, the electrolyte is pressed through the membrane or possibly pressed through capillary gaps during pressure equalization. This can lead to an endangerment of the user, damage to the measuring device and to irreversible changes of the membrane.

The change of the measuring electrode membrane, in turn, causes the measured values to be incorrect and can lead to a complete loss of sensitivity. If the membrane withstands the liquid pressure, then it can nonetheless be deformed so that the diffusion characteristics and therefore the measuring quality change.

SUMMARY OF THE INVENTION

It is an object of the invention to improve an electrochemical measuring cell of the kind described above so that an effective pressure equalization is possible between the electrolyte chamber and the ambient with a simple assembly of the housing.

The advantage of the invention is seen essentially in that breakthroughs are provided over the entire length of the housing. A pressure equalization takes place via the breakthroughs between the electrolyte chamber and the ambient without the electrolyte itself leaking to the ambient. Substantially independently of the built-in position of the sensor or of the location at which the sensor operates, a gas bubble formed in the electrolyte with high probability always finds a location at which a connection between the electrolyte chamber/gas bubble to the ambient is made. In this way, an effective pressure equalization is ensured without an additional mechanically complex pressure equalizing device.

Compared to the state of the art, the membrane itself is no longer subjected to the pressure load which would develop if a difference pressure would occur across the membrane as a consequence of pressure differences between the electrolyte chamber and the ambient. The breakthroughs are advantageously provided with respective stops made of porous sintered polytetrafluoroethylene. The stop is placed in the particular breakthrough in the manner of a plug and is secured therein. The polytetrafluoroethylene rejects liquid and permits a pressure equalization between a gas bubble in the electrolyte chamber and the ambient as a consequence of its open-pore structure.

It is especially advantageous when the housing jacket of the measuring cell is itself made of a material of porous sintered polytetrafluoroethylene. The entire housing jacket therefore contains a plurality of breakthroughs and acts as a block with respect to the electrolyte because of its hydrophobic, open-pore structure. However, it operates as a passthrough for gas for the purpose of providing pressure equalization between the electrolyte chamber and the ambient. The porous housing wall made of PTFE now permits the gas bubble to come into contact with the ambient at any desired location within the electrolyte chamber for the purpose of equalizing pressure. There is practically no location on the housing wall at which there is not a sufficient number of pores which can provide the required pressure equalization.

For a precise and reliable measurement, it is necessary that the electrolyte remain in liquid contact-as unimpeded as possible and for each position with the measuring electrode and the counter electrode and, if required, with a reference electrode. On the other hand, it is advantageous to protect the housing of the measuring cell against mechanical deformation and to maintain the housing stable. Both requirements are realized in an innovative manner in that the electrolyte chamber contains a solid porous filler which, on the one hand, is saturated with the electrolyte and, on the other hand, lies in contact engagement with the inner wall surface of the housing jacket as well as against the flat counter electrode and against the surface of the diffusion membrane facing toward the electrolyte chamber. The diffusion membrane, in turn, carries a metallic-coating which serves as a measuring electrode. The porous filler then serves, on the one hand, as an electrolyte reservoir from which sufficient electrolyte liquid is available for wetting the measuring electrode as well as the counter electrode in each operating position of the measuring cell and can be resupplied or exchanged after appropriate use. On the other hand, the filler supports the wall of the housing jacket and the flat electrode membranes with respect to each other. Sintered glass has been shown to be a suitable material for the filler.

For the case wherein a reference electrode is utilized for the measurement for stabilizing the reference potential, the reference electrode can be placed in a cavity of the filler which extends up to the region of the center of the body of the filler. The reference electrode can be applied to the base of the cavity. The cavity is configured in the form of a blind bore and the opening of the blind bore faces toward the counter electrode in the hollow body. The reference electrode can be made of a fine precious metal wire which is fixed by glass wool in the cavity.

The outer surface of the porous filler is in contact with the inner surface of the housing wall in the electrolyte chamber. This outer surface is provided with recesses which are partially filled with the electrolyte. The recesses act as an additional liquid reservoir from which the porous filler can be filled. In total, the capacity of the electrolyte chamber is increased by the recesses without giving up the desired advantages of the fixed porous filler.

A simple assembly of an electrochemical measuring cell with few components, which are easy to manipulate, results because the housing jacket has a cylindrical form and because its end openings are each provided with an electrode carrier. The electrode carriers clamp respective diffusion membranes to the housing jacket. The membranes, in turn, have surfaces facing toward the electrolyte chamber. These surfaces define the measuring electrode and the counter electrode, respectively. Each of the membranes is clamped to one of the end faces of the filler body by the electrode carrier via a formed-fabric layer. One of the electrode carriers is provided with a diffusion opening accessible to the gas constituent to be detected. The measuring electrode is disposed at the location where the diffusion opening is provided.

As mentioned, the housing jacket is made of porous PTFE and is provided with breakthroughs and stops. In order to protect this housing jacket from damage and contamination, it is surrounded by a gas-impermeable sleeve. The sleeve, however, leaves open the diffusion path between the housing jacket and the ambient at selected locations. This sleeve can be a plastic foil which lies tightly against the housing or the sleeve is formed from a shrink sleeve pulled over the housing jacket. A few openings are provided at freely selectable locations on the sleeve or shrinkage sleeve through which the diffusion path between electrolyte chamber and ambient is maintained. In a limited case, only one opening is provided. When the housing jacket is provided with breakthroughs, the openings in the sleeve correspond thereto or, when the housing jacket is made of porous PTFE, the opening can be provided at any desired location because the diffusion is unimpaired within the housing jacket and the diffusing gas can penetrate from any location of the housing jacket to the opening in the sleeve which is provided in order to communicate with the ambient. In this way, a stable tight configuration is provided which nonetheless can be produced with few components and with simple manufacturing steps.

BRIEF DESCRIPTION OF THE DRAWINGS

The invention will now be described with reference to the drawings, wherein.

DESCRIPTION OF THE PREFERRED
EMBODIMENTS OF THE INVENTION

Figure 1:
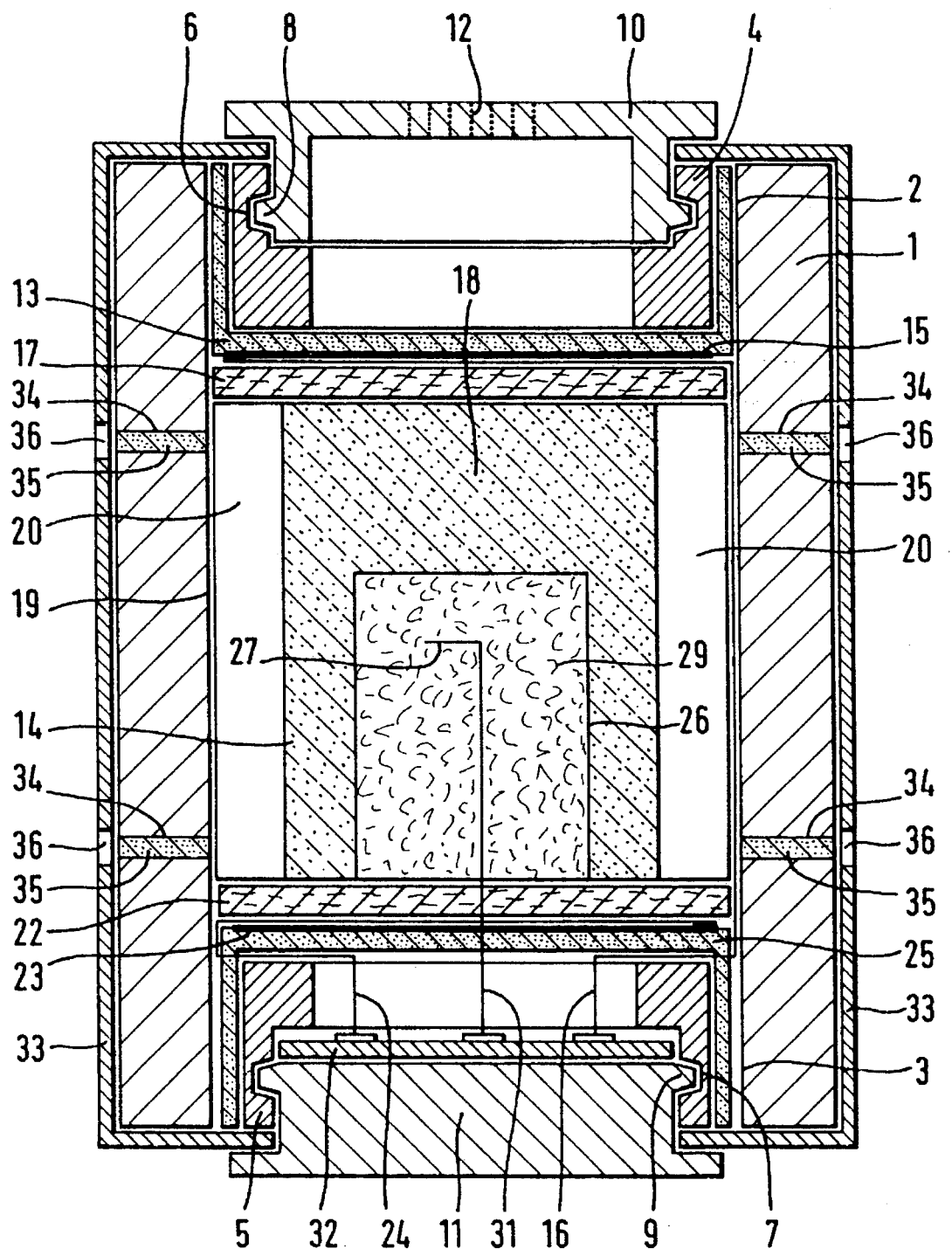
FIG. 1 shows an electrochemical measuring cell according to a first embodiment of the invention wherein the housing jacket is made of nonporous material; and, FIG. 2 shows an electrochemical measuring cell according to a second embodiment wherein the housing jacket is made of porous material.

FIG. 1 shows an electrochemical measuring cell having a cylindrical housing jacket 1 on which the remaining components are mounted. The housing jacket 1 has two end openings (2, 3) and ring-shaped electrode carriers (4, 5) are attached at the end openings (2, 3), respectively. A latch recess (6 or 7) is provided at the inner surface of each electrode carrier (4 or 5). A latch (8 or 9) fitting the latch recess (6 or 7) is provided for latching a cover 10 or a connector 11. The cover 10 acts as a diffusion barrier for the gas to be detected and contains a plurality of diffusion paths 12 which can be configured as capillaries or as porous openings. The electrode carrier 4 clamps a diffusion membrane 13 between itself and the housing jacket 1. The diffusion membrane 13 extends over the entire clear opening of the ring-shaped electrode carrier 4 and the diffusion membrane lies opposite to and is exposed to the diffusion paths 12 of the cover 10. The membrane 13 partitions the ambient from the electrolyte chamber 14 enclosed in the housing jacket 1. The membrane 13 is permeable for the gas to be detected but is impermeable to the electrolyte disposed in the electrolyte chamber 14.

A metallic coating 15 is provided on the surface of the membrane 13 facing toward the electrolyte chamber 14. This coating 15 functions as a measuring electrode and is provided with a contact lead 16. The surface electrode 15 extends essentially likewise over the entire region of the clear opening which lies exposed to the cover 10 by means of the ring-shaped electrode carrier 4. Viewed in the direction toward the electrolyte chamber 14, the metallic coating 15 is covered by a formed-fabric layer 17 which ensures that the electrolyte liquid held in the electrolyte chamber 4 covers the entire electrode surface 15 as uniformly as possible. The electrolyte chamber 14 is essentially completely filled out by a porous fill body or filler 18 which consists of sintered glass. The filler 18 has recesses 20 at its outer surface facing toward the inner wall 19 of the housing jacket 1. The recesses 20 act as an electrolyte reservoir.

The two end faces of the filler body 18 lie against the formed-fabric layer 17, on the one hand, and against a formed-fabric layer 22, on the other hand. The formed-fabric layer 22, in turn, covers a metallic coating 23 in the form of a counter electrode on the membrane 25. The porous filler 18 is filled with electrolyte liquid and so defines the electrolyte bridge between the measuring electrode 15 and the counter electrode 23. The counter electrode 23, in turn, is provided with a contact lead 24. The electrode carrier 5 is secured in the housing jacket 1 and acts to fixedly position the electrode membrane 25 on which the counter electrode 23 is applied as a metallic coating.

A cavity 26 is provided in the interior of the porous filler 18. The cavity 26 starts as a blind bore from one end face of the filler 18 and extends into the center of the filler. The cavity 26 preferably extends from that end face of the filler 18 which lies opposite the counter electrode 23.

A lead-shaped reference electrode 27 is embedded in the cavity 26 at the elevation of the base of the blind bore. The remaining volume of the cavity 26 is filled with glass wool 29. The electrodes (15, 23, 27) are connected to a circuit board 32 via their respective contact leads (16, 24, 31).

Preamplifiers, signal processing devices and other electronic components are built into the circuit board 32. The circuit board 32 is located at the upper face of the connector 11. The circuit board 32 has a connecting strip (not shown) for the necessary connecting contacts for supplying the measuring cell or for conducting away the preprocessed signals.

The surfaces of the electrode carriers (4, 5) close off the housing jacket 1 and are flush therewith. The housing jacket 1 as well as the surfaces of the electrode carriers (4, 5) are joined to each other via a gas-impermeable casing in the form of a shrunk-on sleeve 33 and are thereby pressed tightly against each other. On the one hand, the individual components are pressed tightly against each other and, on the other hand, a gas-impermeable seal of the outer walls is provided.

Several breakthroughs 34 are provided in that portion of the wall of the housing jacket 1 which communicates with the electrolyte chamber 14 in order to maintain pressure equalization between the electrolyte chamber 14 and the ambient. The breakthroughs 34 are provided with respective stops 35 which are permeable to gas but impermeable to the electrolyte. In the simplest case, the stop 35 consists of sintered polytetrafluoroethylene (PTFE). Corresponding jacket openings 36 are provided as an extension of the breakthroughs 34 in order to ensure the exchange of gas between the electrolyte chamber and the ambient through the sleeve 33.

Figure 2:
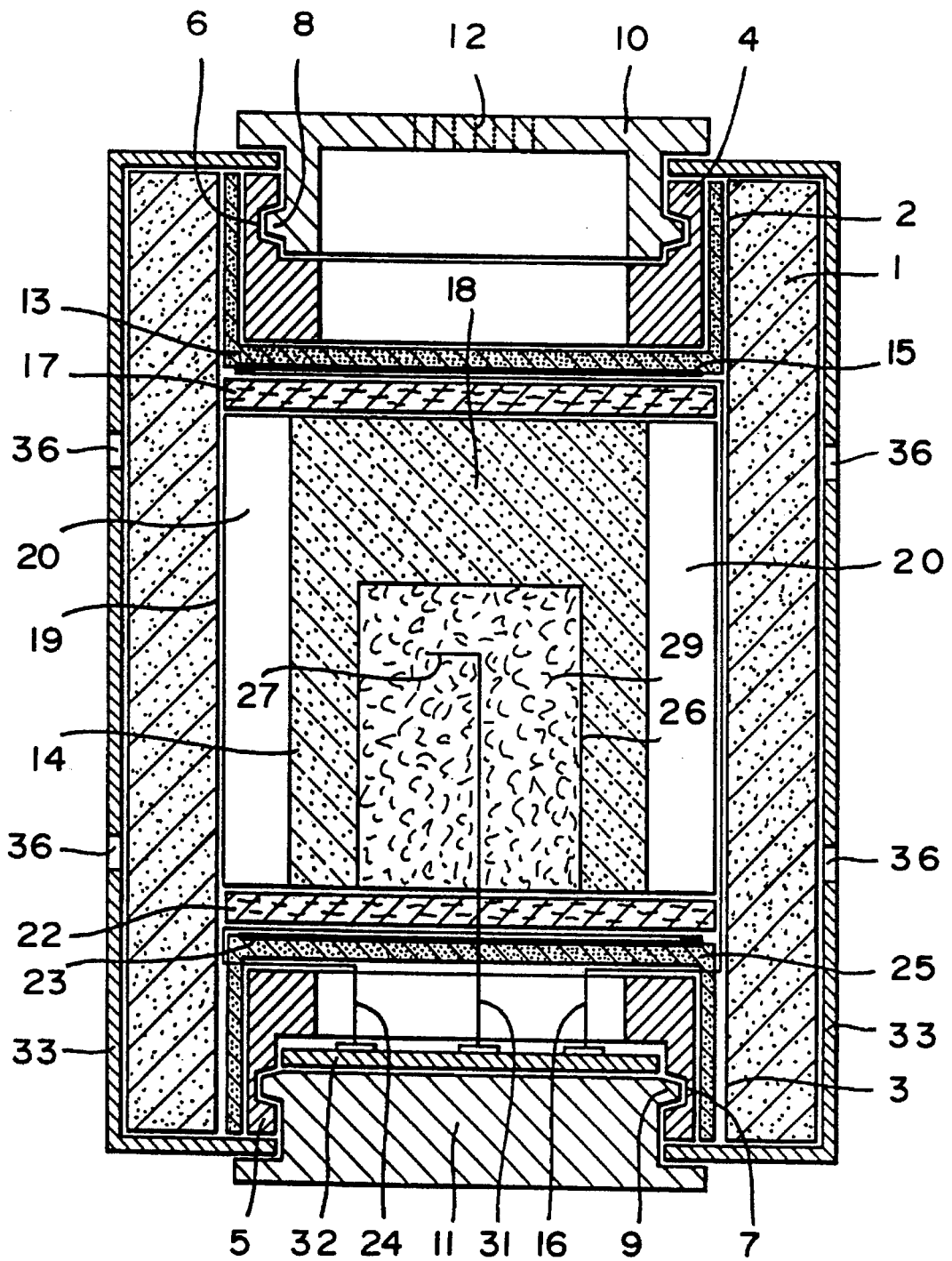

For the case that the housing jacket 1 is produced entirely of porous PTFE as shown in FIG. 2, individual breakthroughs 34 can be omitted; however, one or several openings 36 in sleeve 33 have to be provided at suitable locations. The diffusion of gas from the electrolyte chamber 14 into the ambient can penetrate from the entire surface of the inner wall 19 of the housing jacket 1 through the jacket 1 and exit at the openings 36. The location as to where jacket openings 36 are provided is important only as to where they would be viewed suitable in the context of manufacture.

The elements making up the electrochemical measuring cell are shown in spaced relationship to each other for the sake of clarity. In reality, however, all components are pressed one against the other at their surfaces so as to be in tight mutual contact in order to ensure a tight and leakage free assembly of the individual parts.

It is understood that the foregoing description is that of the preferred embodiments of the invention and that various changes and modifications may be made thereto without departing from the spirit and scope of the invention as defined in the appended claims.

What is claimed is:

1. An electrochemical measuring cell for detecting gaseous constituents in a gas present in the ambient, the measuring cell comprising:

a housing assembly;

an electrolyte;

a measuring electrode and a counter electrode disposed in said housing;

said housing assembly including a housing jacket defining an interior chamber partially filled with said electrolyte so as to leave a gas bubble in the remainder of said chamber thereby allowing said electrolyte to expand and contract in volume in response to changes in ambient conditions;

said housing assembly including first and second holder units for holding said measuring and said counter electrodes, respectively, in liquid contact with said electrolyte;

a gas permeable, electrolyte impermeable membrane interposed between said measuring electrode and said first holder unit so as to delimit said electrolyte chamber;

diffusion means for facilitating the passage of said gaseous constituents from the ambient to said gas permeable membrane; and, said housing jacket defining an inner wall surface and being impermeable to said electrolyte and said housing jacket being made entirely of porous material so as to permit a diffusion of gas through said housing jacket between said remainder of said electrolyte chamber and the ambient thereby equalizing the pressure between said chamber and the ambient.

2. The electrochemical measuring cell of claim 1, said housing jacket being made of sintered polytetrafluoroethylene.

3. The electrochemical measuring cell of claim 2, further comprising a filler body disposed in said electrolyte chamber; said filler body being made of a porous material so as to be saturated by said electrolyte; said second holder unit having a flat surface for holding said counter electrode thereon; said membrane likewise having a flat surface; said measuring electrode being a coating formed on said flat surface of said membrane; and, said filler body being held in said chamber tightly against said flat surfaces and said inner wall surface.

4. The electrochemical measuring cell of claim 3, said filler body consisting of sintered glass.

5. The electrochemical measuring cell of claim 4, said filler body having a cavity formed therein extending inwardly to the region of the center of said filler body to form a base; and, said measuring cell further comprising a reference electrode mounted in said cavity near the base of said cavity.

6. The electrochemical measuring cell of claim 4, said filler body having an outer surface facing toward said inner wall surface of said housing jacket and having a plurality of recesses formed in said outer surface and open to said inner wall surface.

7. The electrochemical measuring cell of claim 3, said housing jacket having a cylindrical shape defining a longitudinal axis and having first and second end openings on said axis; said filler body having first and second end faces transverse to said longitudinal axis; said first and second holder units being mounted in said first and second end openings, respectively; said gas permeable membrane being a first membrane and said measuring cell further comprising a second membrane; said first and second membranes being clamped in against said housing jacket by said first and second holder units, respectively, so as to delimit said electrolyte chamber at said first and second end openings; said first and second membranes defining first and second membrane surfaces facing into said chamber; a first formed fabric layer interposed between said first membrane and said first end face of said filler body and a second formed fabric layer interposed between said second diffusion membrane and said second end face of said filler body; and, said first and second holder units being fitted into said first and second end openings, respectively, of said housing jacket for clamping said formed fabrics against respective ones of said end faces of said filler body; and, said diffusion means being formed in said first holder unit so as to communicate with said gas permeable membrane.

8. The electrochemical measuring cell of claim 1, further comprising a gas-impermeable sleeve surrounding said housing jacket; and, said sleeve having openings formed therein to communicate with said housing jacket.

9. The electrochemical measuring cell of claim 8, said sleeve being a shrink sleeve.

10. The electrochemical measuring cell of claim 1, said porous material being porous polytetrafluoroethylene.

* * * * *